(12) United States Patent
Schnell et al.

(10) Patent No.: US 11,324,905 B2
(45) Date of Patent: May 10, 2022

(54) BENDABLE TRACHEAL VENTILATION APPARATUS

(71) Applicant: TRACOE MEDICAL GMBH, Nieder-Olm (DE)

(72) Inventors: Ralf Schnell, Selingenstadt (DE); Andreas Hahn, Saulheim (DE)

(73) Assignee: TRACOE MEDICAL GMBH, Nieder-Olm (DE)

( * ) Notice: Subject to any disclaimer, the term of this patent is extended or adjusted under 35 U.S.C. 154(b) by 448 days.

(21) Appl. No.: 16/345,143

(22) PCT Filed: Oct. 25, 2017

(86) PCT No.: PCT/EP2017/077262
§ 371 (c)(1),
(2) Date: Apr. 25, 2019

(87) PCT Pub. No.: WO2018/082982
PCT Pub. Date: May 11, 2018

(65) Prior Publication Data
US 2019/0282775 A1   Sep. 19, 2019

(30) Foreign Application Priority Data
Nov. 2, 2016   (DE) .......................... 102016120822.1

(51) Int. Cl.
*A61M 16/04*   (2006.01)
(52) U.S. Cl.
CPC .... *A61M 16/0445* (2014.02); *A61M 16/0402* (2014.02); *A61M 16/0418* (2014.02); *A61M 16/0465* (2013.01); *A61M 16/0434* (2013.01)

(58) Field of Classification Search
CPC .......... A61M 16/0445; A61M 16/0402; A61M 16/0465; A61M 16/0434; A61M 16/0418; A61M 16/0479; A61M 16/0481
See application file for complete search history.

(56) References Cited

U.S. PATENT DOCUMENTS 4,852,564 A * 8/1989 Sheridan ................ A61M 16/04
                                                          128/202.27
4,987,895 A   1/1991 Heimlich
(Continued)

FOREIGN PATENT DOCUMENTS

CN    201414982    3/2010
CN    103656821    3/2014
(Continued)

OTHER PUBLICATIONS

German Search Report dated Jun. 19, 2017.

*Primary Examiner* — Douglas Kay
(74) *Attorney, Agent, or Firm* — Holzer Patel Drennan (57) ABSTRACT

The present invention relates to a tracheal ventilation apparatus, in particular a tracheostomy cannula or an endotracheal tube, having a cannula tube, which from a point of view from a gas supply, has a proximal tube portion with a proximal opening and a distal tube portion with a distal opening. In order to provide an easy-to-handle tracheal ventilation apparatus that can easily be inserted and that impedes a swallowing process as little as possible, the proximal tube portion and the distal tube portion are connected to one another by way of an axially air-permeable joint that facilitates at least restricted mobility and, in particular, pivotability of a longitudinal axis of the distal tube portion with respect to a longitudinal axis of the proximal tube portion.

23 Claims, 7 Drawing Sheets

(56) References Cited

U.S. PATENT DOCUMENTS

| | | | | | |
|---|---|---|---|---|---|
| 5,251,619 | A | * | 10/1993 | Lee | A61B 5/14542 128/207.15 |
| 5,536,235 | A | * | 7/1996 | Yabe | A61B 1/00071 138/118 |
| 6,155,252 | A | * | 12/2000 | Warters | A61M 16/042 128/200.24 |
| 2002/0043266 | A1 | | 4/2002 | Toti et al. | |
| 2003/0136413 | A1 | | 7/2003 | Brain | |
| 2010/0163050 | A1 | * | 7/2010 | Hoffa | A61M 16/0465 128/207.14 |
| 2011/0048427 | A1 | * | 3/2011 | Zachar | A61L 29/085 128/207.15 |
| 2011/0230742 | A1 | * | 9/2011 | Finneran | A61B 5/6885 600/364 |
| 2012/0241084 | A1 | * | 9/2012 | Nasir | A61M 16/0402 156/242 |
| 2013/0000649 | A1 | | 1/2013 | Hayman | |
| 2016/0175549 | A1 | * | 6/2016 | Nelson | A61M 16/0057 128/207.15 |
| 2016/0256650 | A1 | * | 9/2016 | Wang | A61M 16/0481 |
| 2018/0172189 | A1 | * | 6/2018 | Hobbs | F16L 47/32 |

FOREIGN PATENT DOCUMENTS

| | | | |
|---|---|---|---|
| DE | 2553307 | 6/1976 | |
| DE | 102006035887 | 2/2008 | |
| RU | 024153 B1 * | 8/2016 | F16L 11/20 |
| WO | 2006100424 | 9/2006 | |
| WO | 2010062603 | 6/2010 | |
| WO | 2013109569 | 2/2013 | |

\* cited by examiner

BENDABLE TRACHEAL VENTILATION APPARATUS

BACKGROUND

1. Field of the Invention

The present invention relates to a tracheal ventilation apparatus, in particular a tracheostomy cannula or an endotracheal tube, having a cannula tube, which has a proximal tube portion with a proximal opening and a distal tube portion with a distal opening.

2. Relevant Background

Tracheal ventilation apparatuses of this type are introduced into the trachea of a patient in order to supply the patient with air or respiratory gas. The proximal end of the tracheal ventilation apparatus can be connected to a ventilation apparatus outside the patient, while the distal end of the tracheal ventilation apparatus can be inserted into the trachea. The cannula tube connecting the two openings serves for the passage of the respiratory gas (respiratory air). In the case of a tracheostomy cannula, the cannula is inserted through an artificially produced opening into the trachea of a patient. In the case of an endotracheal tube, said cannula is introduced into the trachea via the mouth and pharynx. The problems discussed here occur in the case of both types of tracheal tubes, but principally in the case of tracheostomy cannulas. In order to use tracheostomy cannulas, an opening (stoma) is created from the neck to the trachea. The tracheostomy cannula is inserted into said opening, wherein the cannula extends from the outer side of the patient neck into the trachea in an arc comprising approximately 90°. Since the anatomy of each patient is different, fitting problems can occur here, which lead, for example, to the distal end of the cannula rubbing against the trachea wall.

A further problem is that a tracheal ventilation apparatus introduced into the trachea generally impedes the swallowing process of a patient, since the larynx is slightly raised and lowered with the trachea for swallowing. The weight, shape and size of the tracheal ventilation apparatus, however, limit the mobility of the trachea and the larynx. If the tracheal ventilation apparatus is non-resilient or made of a hard material, there is the risk that the distal end of the tracheal ventilation apparatus presses against the trachea wall during swallowing. This can lead to necroses and bleeding. In order to avoid such effects, there are very soft tracheostomy cannulas. In the case of such soft tracheal ventilation apparatuses, insertion into the trachea is usually laborious. The tracheal ventilation apparatus can bend or rotate and the cannula tip can be arranged at an unfavourable angle on the tracheal wall and rub against it. As a result, the trachea can be damaged. In the worst case, it can even happen with soft cannulas that the cannula is not inserted in the direction of the lungs during insertion but is incorrectly inserted in the direction of the mouth.

SUMMARY

Against this background, it is an object of the present invention to provide an easy-to-handle tracheal ventilation apparatus that can easily be inserted and that impedes a swallowing process as little as possible, in which the risk of injuring the tracheal wall is reduced.

According to the invention, the object is achieved by a tracheal ventilation apparatus of the type mentioned in the introduction, wherein the proximal tube portion and the distal tube portion are connected to one another by way of an axially air-permeable joint that facilitates at least restricted mobility and, in particular, pivotability of the axis of the distal tube portion with respect to the axis of the proximal tube portion.

The proximal tube portion and the distal tube portion can be moved relative to one another by means of the joint, i.e. the axes of the two cannula portions can be pivoted and can be adjusted at different relative angles. The central longitudinal centre lines of the tubular cannula portions are referred to here as the axis which can also be curved in an arc shape and which would smoothly merge into one another without a joint between the proximal and the distal portion and would possibly merge into one another without a bend in a slight curvature, wherein the joint is intended to permit a relative pivoting or slight bend of the axis profile with a comparatively small radius of curvature, which is less than half, preferably less than one fifth of the other minimum radius of curvature of the cannula tube. The distal tube portion can thus be pivoted in different directions relative to the proximal tube portion. During the insertion of the tracheal ventilation apparatus into the trachea and also afterwards, the proximal tube portion can move together with the larynx and the trachea, without the distal tube portion of the cannula tube pressing against the wall of the trachea or rubbing against the latter. The articulated connection of the proximal tube portion to the distal tube portion increases the mobility of the tracheal ventilation apparatus and facilitates swallowing.

The terms 'distal' and 'proximal' are used in the context of the present invention from the point of view of a treating doctor, i.e. that the proximal end of the tracheal ventilation apparatus or cannula tube lies outside the patient's body, while the distal end lies in the interior of the trachea when the tracheal ventilation apparatus is in the inserted state.

In one embodiment, the cannula tube has a fillable cuff on its outer periphery for sealing and soft fixing of the cannula tube in the trachea, wherein the joint is arranged in a region which is delimited by the outer distal and proximal fastening edges of the cuff.

A cuff usually consists of an inflatable, very thin-walled sleeve, the end portions of which rest on the outside of the cannula tube and are attached there, and which has a clear over-dimension at least in a central portion relative to the cannula tube or can be inflated to such an over-dimension so that this portion can be inflated after insertion of the cannula into the trachea and comes into contact with the wall of the trachea along its circumference in a sealing manner and with preferably low pressure. The end portions, which generally represent sleeve portions (also referred to here as 'neck portions'), are typically adhesively bonded or welded to the outer wall of the cannula tube over their length and their circumference. The axially outer edges of these end portions then form the region defined above for a preferred arrangement of a joint.

In one embodiment, the fillable cuff has a central portion and a portion adjoining the central portion proximally and/or distally with a greater wall thickness than the central portion, wherein the wall thickness of the portion adjoining the central portion proximally and/or distally is preferably 50% to 300% greater than the wall thickness of the central portion. The portions adjoining the central portion proximally and/or distally enclose the cuff volume together with the central portion. The portions adjoining the central portion proximally and/or distally can have an outer diameter, which decreases from the central portion in the direction of the ends of the cuff. In a state in which the cannula tube is inserted into a trachea and the cuff is filled with a fluid, the locally increased wall thickness limits the deflection of the distal end of the cannula tube and supports the movement of the joint, preventing the end portion of the tube abutting the inner wall of the trachea.

In one embodiment, the proximal and the distal tube portion are spaced from one another by an annular gap with a clear gap width d and connected to one another by way of the axially air-permeable joint which bridges the gap.

In one embodiment, the annular gap is located in an axial region of a distal or proximal neck portion of a cuff. That is to say, the end or neck portion of the cuff connects the proximal and distal tube portions to one another and either acts as a joint itself or comprises a corresponding joint. The wall thickness and elasticity of the neck portion must be adjusted for this purpose where required.

The joint is preferably adhesively bonded, welded and/or injection-moulded to the proximal tube portion and/or the distal tube portion. So that no respiratory gas can escape through the articulated connection, in one embodiment, the joint is connected to the proximal tube portion and the distal tube portion in a gas-tight manner. The joint is preferably radially air-impermeable.

In one embodiment, the distal tube portion has a maximum bending angle relative to the axis of the proximal tube portion via the joint in a range of at least +10° to −10°, preferably a range of +25° to −25°, in any direction relative to the cannula axis.

It is advantageous if the joint is designed in such a way that the joint angle between the proximal tube portion and the distal tube portion can be changed by 10° using a force F, which is reduced by more than 70%, as it has to be rotated in order to bend the proximal tube portion by 10° without a joint. A joint designed in this way is flexible enough to not impede a swallowing process and still be sufficiently rigid, in order to enable a simple insertion of the tracheal ventilation apparatus into a trachea.

In one embodiment, both the cannula tube, i.e. the proximal and distal tube portions thereof, and the joint are made of plastic, wherein the joint is made from a plastic which has a lower shore hardness than the plastic of the cannula tube. The plastic of the joint with the lower shore hardness than the plastic of the cannula tube is softer and therefore more easily deformable and, in this way, enables movement of the joint between the proximal and the distal tube portion. The tube portions made from a harder plastic than the plastic of the joint are rigid enough to be easily inserted into the trachea of a patient. The tube portions made of a harder plastic preferably have a shore A hardness of 50 to 98. The comparatively softer plastic of the joint has a shore A hardness that is at least 50% lower.

The corresponding joint mobility can also be achieved with the same plastic material as is used for the proximal and distal tube portions, which, however, has a smaller wall thickness in the intended joint region. The wall thickness of the proximal and distal tube portions is preferably between 0.8 mm and 1.8 mm. In contrast, the wall thickness of the joint is preferably between 0.1 mm and 0.4 mm. If the joint has a sleeve portion, the wall thickness of the sleeve portion can thus be significantly reduced. For example, the wall thickness of a sleeve portion can be 10 µm.

In one embodiment, the joint is elastically expandable and/or compressible in the axial direction of the cannula tube, wherein the axial gap width d of the annular gap between the proximal tube portion and the distal tube portion predetermines the maximum compressibility. In one embodiment, the gap width d is 1 mm to 10 mm, preferably 2 mm to 4 mm. The compressibility is set such that the distal tube portion is moved in the direction of the proximal tube portion, when the distal tube portion presses against the tracheal wall with a force greater than 0.05 N. The elastic compressibility and expandability can be adjusted by using a correspondingly thin and/or soft joint material. If the distal tube portion abuts the tracheal wall, the joint which can be elastically expanded and/or compressed in the axial direction of the cannula tube reduces a strain on the trachea. If the force acting on the tracheal wall exceeds, for example, 0.05 N, the joint is compressed and the distance between the distal tube portion and the proximal tube portion is reduced. If the force has a component that encloses an angle different from 0° with the central axis of the distal tube portion, so that it does not act perpendicularly on the wall of the trachea, the distal tube portion can bend relative to the proximal tube portion, which is also facilitated by the compressibility.

If such an expandable and/or compressible joint is arranged inside a central cuff, the cuff dampens the relative movement between the proximal tube portion and the distal tube portion. If the proximal tube portion and the distal tube portion are moved towards one another, the cuff volume reduces and the cuff pressure increases. If the distance between the proximal tube portion and the distal tube portion increases, the volume of the cuff expands and the cuff pressure decreases. Conversely, the extension or extent of the elastic contraction of expandable elastic sleeve portions of the joint can also be adjusted by setting the cuff pressure within certain limits.

The cuff pressure enables buffering of the compression of the cannula in the axial direction of the cannula tube. The joint and the cuff, which surrounds the joint and is filled with gas under a slight overpressure, act like a shock absorber, absorbing and reducing impact on the tracheal ventilation apparatus. In this way, damage to the tracheal wall by the distal cannula end can be reduced and the swallowing process can be facilitated. Preferably, pressure of 15 mbar to 30 mbar is applied to a cuff with the aid of air. The cuff, which is arranged radially on the outside of the annular gap, effects a resetting force into the starting position of the joint. At the same time, the filled cuff prevents the ends of the proximal and the distal tube portions located at the gap from pressing against the trachea and damaging it. The cuff cushions the annular gap and the joint of the tracheal ventilation apparatus with respect to the trachea and consequently a flush fixing of a sleeve portion forming the joint to the respective tube portions is not necessary.

In one embodiment, the joint is a sleeve portion which is attached on one side of an annular gap between the proximal and the distal tube portion to the proximal tube portion and on the other side of the gap to the distal tube portion. The plastic of the sleeve portion preferably has a lower shore hardness than the plastic of the cannula tube. The sleeve portion made of the softer plastic is elastically deformable, so that the gap width d, i.e. the clear distance between the proximal tube portion and the distal tube portion, on opposite sides of the tube portions can be changed to different extents and/or in different directions. If the sleeve portion is compressed or expanded on one side, the gap width d of the annular gap is reduced or enlarged accordingly on one side, such that the proximal tube portion and the distal tube portion are pivoted relative to one another.

In one embodiment, the sleeve portion is attached on both sides of the annular gap to the proximal tube portion and the distal tube portion. The sleeve portion is preferably adhesively bonded, welded or injection-moulded onto the end faces of the proximal and the distal tube portions. In another embodiment, the ends of the tube portions facing one another have a fold for flush and smooth reception of the complementarily configured sleeve portion. The sleeve portion connects the proximal tube portion and the distal tube portion like a coupling sleeve for the passage of respiratory gas.

In one embodiment, the joint has a second sleeve portion in addition to the sleeve portion described above, which is arranged concentrically with respect to the first sleeve portion, wherein the first sleeve portion is connected to the proximal tube portion and the distal tube portion radially on the outside, and the second sleeve portion is connected to the proximal tube portion and the distal tube portion radially on the inside. The two sleeve portions connect the proximal tube portion and the distal tube portion both on the inside of the cannula tube, i.e. in the central lumen of the cannula tube, and also on the outer side of the cannula tube. The first sleeve portion and/or the second sleeve portion span the annular gap and are attached on both sides of the annular gap to the proximal tube portion and the distal tube portion. For example, one or both of the sleeve portions are attached to the proximal and distal tube portions by adhesive bonding, welding or injection moulding.

Preferably, the one sleeve portion of the joint, or if the joint consists of two sleeve portions, both sleeve portions, has or have a smaller wall thickness than the average wall thickness of the proximal tube portion in the connection region of the joint. For example, the average wall thickness of the first sleeve portion and/or of the second sleeve portion is ¼ of the average wall thickness of the proximal tube portion in the connection region of the joint.

In one embodiment, the sleeve portion is butt-connected to the ends of the proximal and distal tube portions. The sleeve portion thus fills the annular gap between the proximal tube portion and the distal tube portion. The sleeve portion can adjoin the proximal tube portion and the distal tube portion in a seamless manner. The sleeve portion has a wall thickness in its proximal connection region that corresponds to the wall thickness of the proximal tube portion, and in its distal connection region a wall thickness that corresponds to the wall thickness of the distal tube portion. In a slightly modified embodiment, the sleeve portion has a greater wall thickness than the proximal tube portion and the distal tube portion, each having an annular groove in the end faces of the sleeve portion for receiving the ends of the proximal and distal tube portions in said grooves. The sections of the sleeve portion extending beyond the gap over the axial length of the cannula tube and into the region of the proximal and distal tube portions are attached, preferably adhesively bonded, welded or injection-moulded, on both sides of the gap to the proximal tube portion and the distal tube portion.

In order to stabilise the joint, the joint in one embodiment has a plurality of plastic struts, preferably two diametrically opposite plastic struts, which bridge the annular gap and connect the proximal tube portion to the distal tube portion. The plastic struts are preferably arranged distributed uniformly in the circumferential direction of the annular gap. The arrangement of the plastic struts is suitable for limiting the degrees of freedom of the joint. If the joint has two plastic struts, for example, which are arranged at an angular distance of 180° or even slightly less in the circumferential direction of the annular gap, the joint, similar to a hinge joint, has a preferred pivoting direction approximately parallel to the plastic struts. In one embodiment, the struts are arranged laterally, so that the bending angle of the cannula tube can be increased or reduced by means of the joint, and the ability to bend in a lateral direction is additionally reduced. The plastic struts can be made from the same plastic as the tube portions or from a softer plastic than this. At the same time, the joint is reinforced against axial forces by the struts.

In one embodiment, the axial gap width d of the annular gap is 1 mm to 10 mm, preferably 3 mm to 4 mm. Such gap widths prevent the central lumen of the cannula tube from closing in the event of maximum joint movement and breathing through the tracheal ventilation apparatus from being made substantially more difficult.

In one embodiment, the joint is formed from a wall section of the cannula tube which separates the proximal tube portion from the distal tube portion, wherein said wall section has a reduced wall thickness.

Further advantages, features and possible applications of the present invention become clear on the basis of the present description of an embodiment and the associated figures, wherein identical reference signs refer to the same elements.

DETAILED DESCRIPTION

Figure 1:
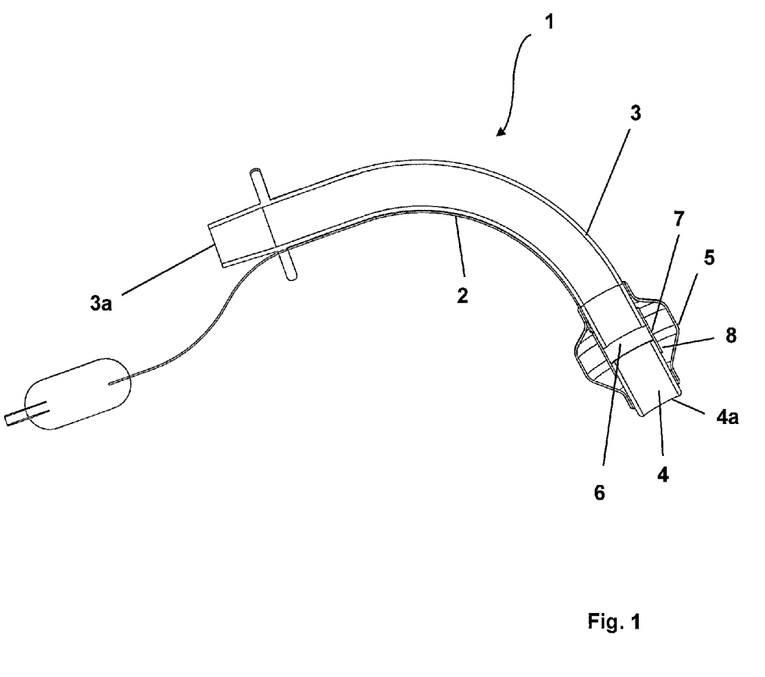
FIG. 1 shows a longitudinal section through a tracheal ventilation apparatus according to an embodiment of the present invention.

FIG. 1 shows a longitudinal section through a tracheal ventilation apparatus 1 according to an embodiment according to the invention. The tracheal ventilation apparatus 1 has a cannula tube 2 made of plastic, which has a proximal tube portion 3 with a proximal opening 3a and a distal tube portion 4 with a distal opening 4a. On its outer periphery, the cannula tube 2 has a cuff 5, which is arranged near the distal end of the cannula tube 2 and is shown in its filled state. The distance between the fillable cuff portion and the distal end of the cannula tube is 3 mm to 8 mm.

At an axial position covered by the cuff 5 and radially inside the cuff 5, an annular gap 6 separates the proximal tube portion 3 and the distal tube portion 4. The axial distance between the proximal tube portion 3 and the distal tube portion 4 corresponds to the width d of the annular gap 6. As can be clearly seen from the detailed view in FIG. 2, the proximal tube portion 3 and the distal tube portion 4 are connected to one another by way of a joint 7. The joint 7 is a sleeve portion 8, which is arranged radially on the outside of the cannula tube 2 and connects the proximal tube portion 3 and the distal tube portion 4. The sleeve portion 8 spans the annular gap 6 and is attached on both side of the gap 6 to the proximal tube portion 3 and the distal tube portion 4. The sleeve portion 8 is adhesively bonded, welded or injection-moulded to the proximal tube portion 3 and the distal tube portion 4.

Figure 2:
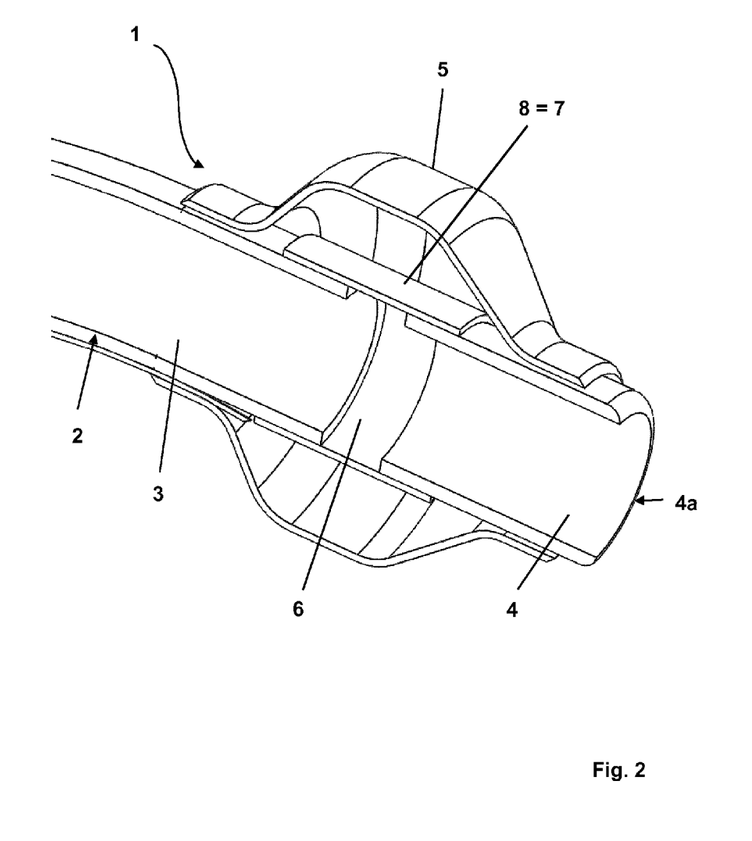
FIG. 2 shows a detailed view of the joint in the embodiment according to FIG. 1.

The sleeve portion 8 is made from a softer plastic than the plastic from which the proximal tube portion 3 and the distal tube portion 4 are made. The wall thickness of the sleeve portion 8 is smaller than the average wall thickness of the proximal tube portion 3 in the connection region of the joint 7.

In the filled state as shown, the cuff 5 cushions the joint 7 thus preventing the joint 7 or the ends of the proximal or distal tube portion 3, 4 adjacent to the annular gap 6 from rubbing against the wall of the trachea in such a way that damage occurs when the tracheal ventilation apparatus 1 is inserted into the trachea of a patient.

Figure 3:
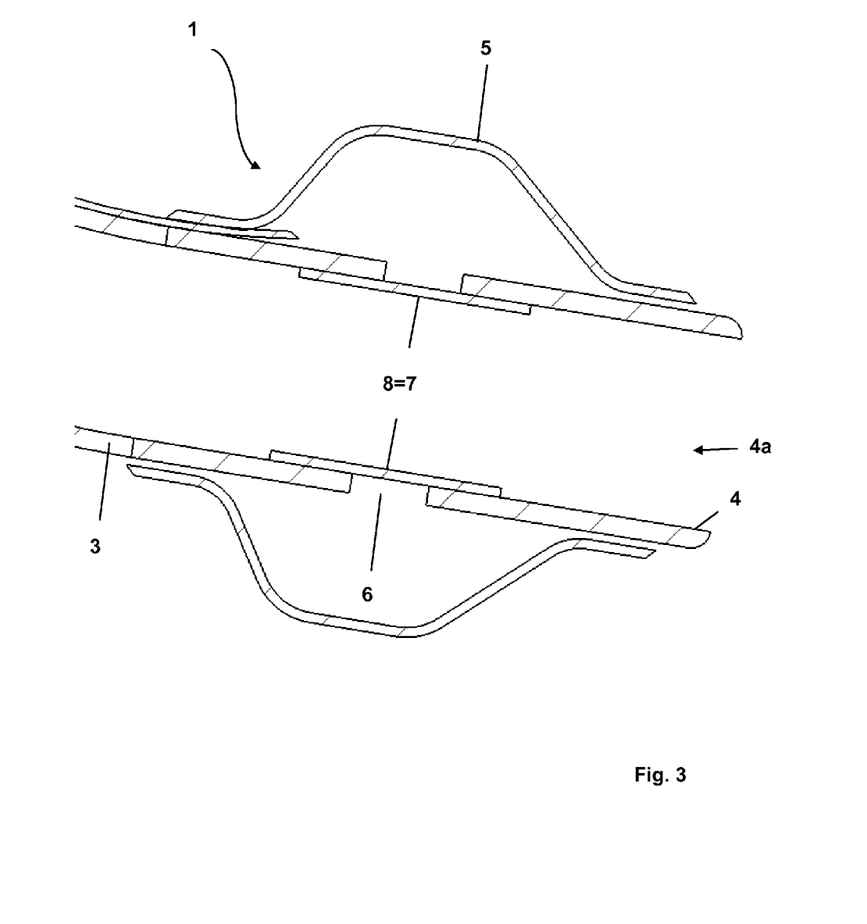
FIG. 3 shows a partial section of the joint in a further embodiment of the present invention.
Figure 4:
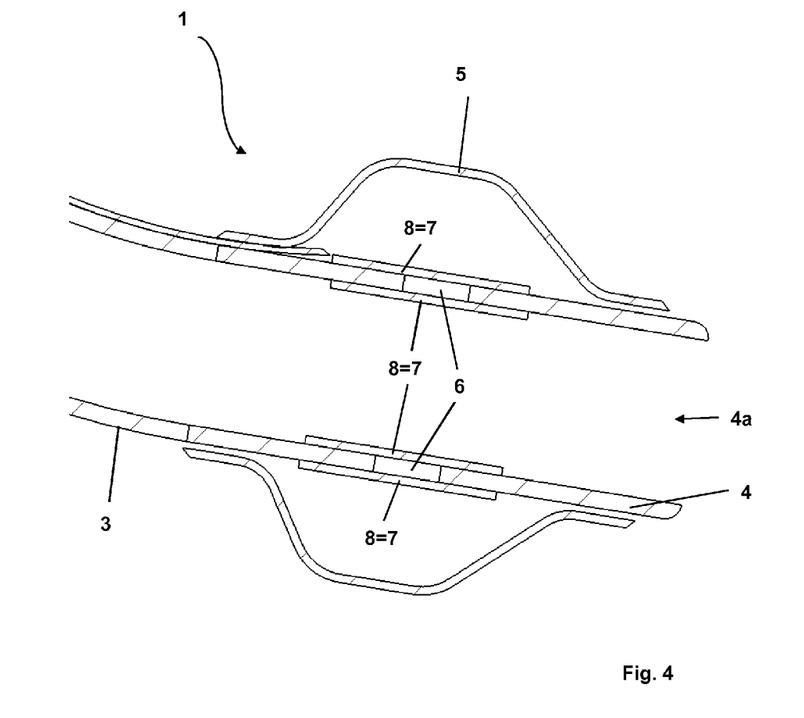
FIG. 4 shows a partial section of the joint in a further embodiment of the present invention.

FIGS. 3 and 4 show alternative embodiments of the present invention in a sectional view. The only difference compared to the embodiment from FIGS. 1 and 2 is the design of the joint 7.

In the embodiment according to FIG. 3, the joint 7 comprises a sleeve portion 8 ('coupling sleeve') which is arranged on the internal side of the cannula tube 2 and connects the proximal tube portion 3 and the distal tube portion 4. The sleeve portion 8 extends beyond the annular gap 6 and is attached on both sides of the gap 6 to the proximal tube portion 3 and the distal tube portion 4 on the internal side of the cannula tube 2. The plastic of the sleeve portion 8 has a lower shore hardness than the plastic from which the proximal and the distal tube portions 3, 4 are made.

The joint 7 in the embodiments according to FIGS. 1 to 3 has exactly one sleeve portion 8, which connects the proximal tube portion 3 and the distal tube portion 4 radially in a gas-tight manner.

The joint 7 according to the embodiment shown in FIG. 4 has exactly two sleeve portions 8, of which a first sleeve portion 8 is arranged radially on the inside and a second sleeve portion 8 is arranged radially on the outside of the cannula tube 2. Both sleeve portions 8 are made of a softer plastic than the proximal and the distal tube portions 3, 4.

As in the previously described embodiments, the sleeve portions 8 extend over the annular gap 6 and are attached on both sides to the proximal tube portion 3 and the distal tube portion 4, so that said sleeve portions form an axially gas-permeable joint 7. The annular gap 6 is not filled and consequently the annular region between the sleeve portions 8 forms a cavity. The joint 7 is radially air-impermeable.

Figure 5:
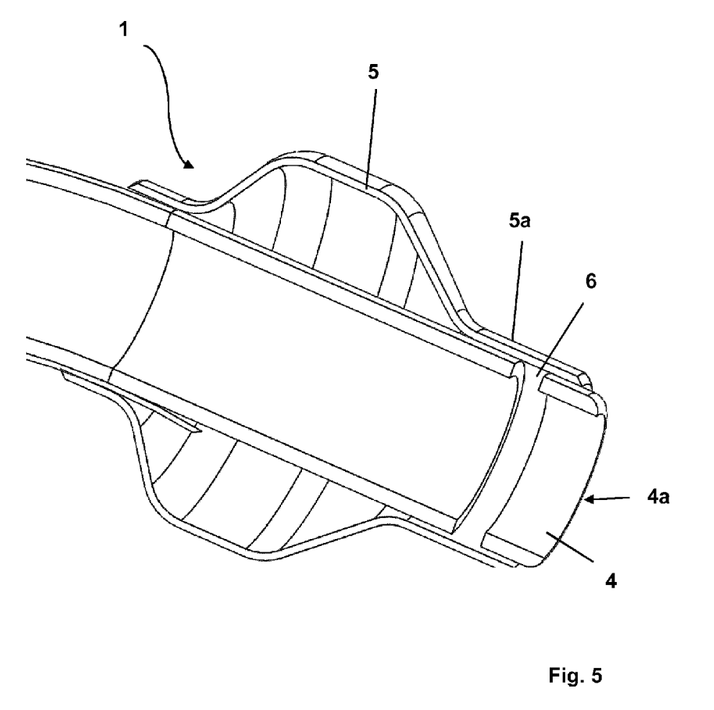
FIG. 5 shows a perspective detailed view of a joint in a further embodiment of the present invention.
Figure 6:
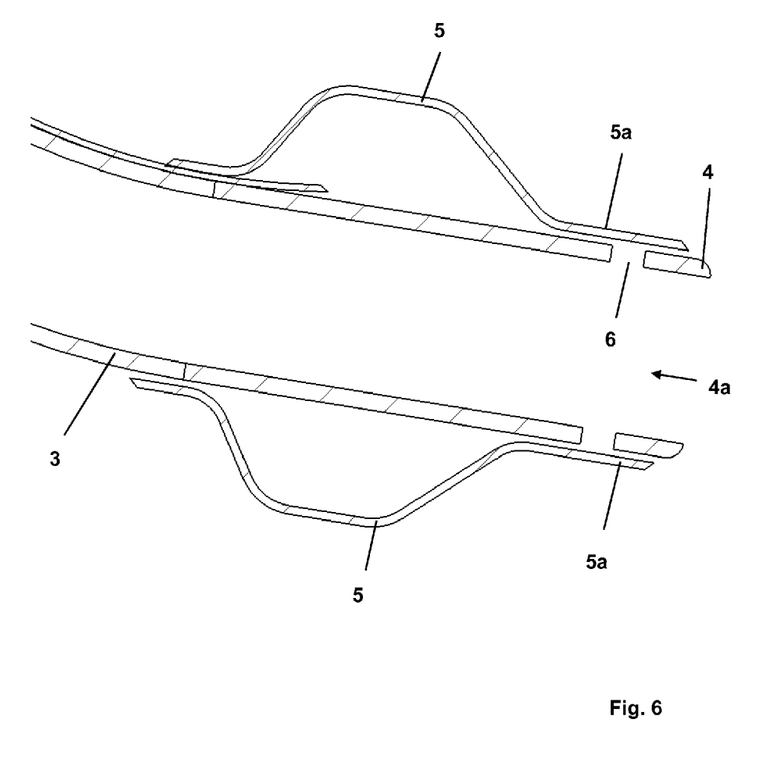
FIG. 6 shows a sectional view of FIG. 5.

FIGS. 5 and 6 show a further embodiment of a tracheal ventilation apparatus 1 according to the invention in a detailed view. The embodiment in FIGS. 5 and 6 differs from the previously described embodiments only in the arrangement of the annular gap 6 and the configuration of the axially gas-permeable joint 7, which connects the proximal tube portion 3 and the distal tube portion 4 in an articulated manner. The annular gap 6 is arranged in an axial region which is covered by a distal neck portion 5*a* of the cuff 5. In this embodiment, the joint 7 is formed by the neck portion 5*a* of the cuff 5. The neck section 5*a* spans the annular gap 6 radially on the outside and is adhesively bonded in a gas-tight manner to the proximal tube portion 3 and the distal tube portion 4 on both sides of the annular gap 6. The cuff 5, including the neck portion 5*a*, is made of a softer plastic than the plastic from which the proximal and the distal tube portions 3, 4 are formed.

Figure 7:
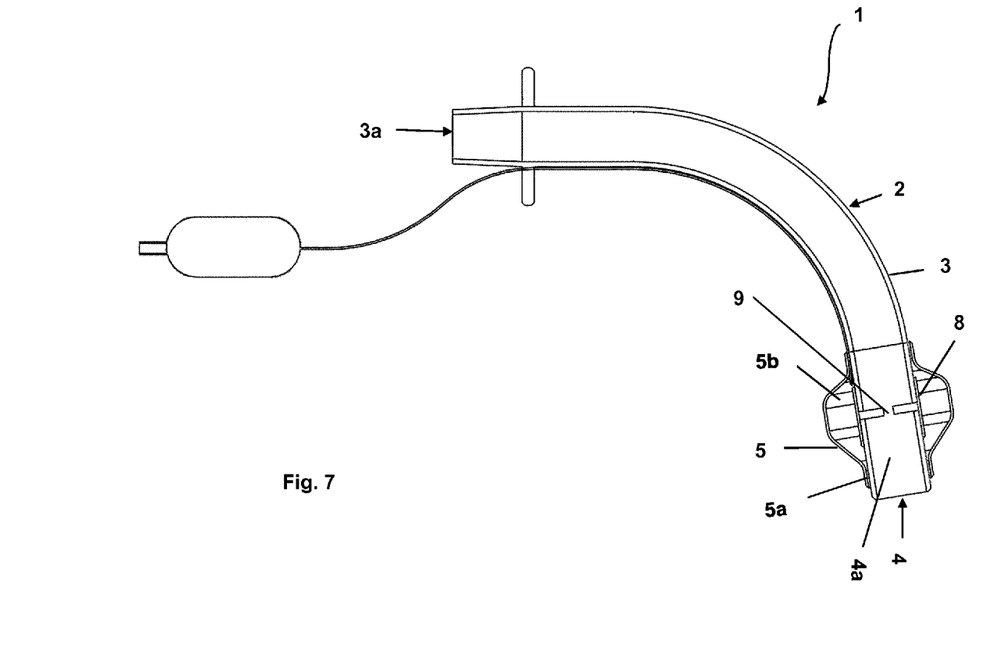
FIG. 7 shows a longitudinal section through a tracheal ventilation apparatus according to a further embodiment of the present invention.

FIG. 7 shows a longitudinal section through a tracheal ventilation apparatus 1 of a further embodiment of the present invention. The tracheal ventilation apparatus 1 differs from the tracheal ventilation apparatuses in the previously described embodiments in the arrangement of the annular gap 6, which separates the proximal tube portion 3 and the distal tube portion 4, and in the design of the joint 7. The annular gap 6 is arranged in an axial region of the cannula tube 2, which is covered by the cuff 5, more precisely by the fillable portion 5*b* of the cuff 5. A sleeve portion 8 is arranged on the radially outer side of the cannula tube 2, which spans the annular gap 6 and is adhesively bonded to the proximal tube portion 3 and the distal tube portion 4 on both sides of the gap 6. The sleeve portion 8 forms the joint 7 that connects the tube portions 3, 4 to one another in an articulated manner. The sleeve portion 8 is made of a softer plastic than the plastic from which the tube portions 3, 4 are made. Two reinforcing struts 9 are arranged diametrically opposite one another in the annular gap 6, which connect the proximal tube portion 3 and the proximal [sic] tube portion 4 in addition to the sleeve portion 8. The reinforcing struts 9 limit the degrees of freedom of the joint 7 and work in such a way that the joint 7 can be moved in a manner similar to a hinge joint.

For the purposes of the original disclosure, it is pointed out that all features, as can be derived from the present description, the drawings and the claims by a person skilled in the art, even if they have been described specifically only in connection with certain additional features, can be combined both individually and in any combination with other features or groups of features disclosed here, insofar as this has not been expressly excluded or technical conditions make such combinations impossible or pointless. A comprehensive explicit presentation of all conceivable combinations of features is dispensed with here only for the sake of brevity and readability of the description.

While the invention has been presented and described in detail in the drawings and the preceding description, such presentation and description are merely exemplary and is not intended to limit the scope of protection, as defined by the claims. The invention is not restricted to the embodiments disclosed.

Modifications of the embodiments disclosed are obvious to a person skilled in the art from the drawings, the description and the attached claims. In the claims, the word 'have' does not exclude other elements or steps, and the indefinite article 'a' or 'one' does not exclude a plurality. The mere fact that certain features are claimed in different claims does not exclude the combination thereof. Reference signs in the claims are not intended to limit the scope of protection.

LIST OF REFERENCE SIGNS

1 Tracheal ventilation apparatus
2 Cannula tube
3 Proximal tube portion
3*a* Proximal opening
4 Distal tube portion
4*a* Distal opening
5 Cuff
5*a* Distal neck portion
5*b* Fillable portion
6 Annular gap
7 Joint
8 Sleeve portion
9 Plastic struts

What is claimed is:
1. A tracheal ventilation apparatus, in particular tracheostomy cannula or endotracheal tube, comprising a cannula tube which, from a point of view from a gas supply, has a proximal tube portion with a proximal opening and a distal tube portion having a distal opening, characterised in that the proximal tube portion and the distal tube portion are connected to one another by way of a joint that permits airflow through between the proximal tube portion and the distal tube portion and facilitates at least restricted mobility and, in particular, pivotability of a longitudinal axis of the distal tube portion with respect to a longitudinal axis of the proximal tube portion, wherein the proximal and distal tube portions are spaced apart from one another by an annular gap having a gap width and are connected to one another by way of the joint that bridges the gap, wherein the joint is formed by a sleeve portion having a smaller wall thickness than an average wall thickness of the proximal tube portion in a connection region of the joint.

2. The tracheal ventilation apparatus according to claim 1, characterised in that the cannula tube has a fillable cuff on its outer periphery for sealing and soft fixing the cannula tube in a patient's trachea, wherein the joint is arranged in a region, which is delimited by outer distal and proximal fastening edges of the cuff.

3. The tracheal ventilation apparatus according to claim 2, characterised in that the cuff has a central portion and a portion which adjoins the central portion that has a greater wall thickness than the central portion.

4. The tracheal ventilation apparatus according to claim 2, wherein the cuff comprises a non-inflatable distal neck portion, characterised in that the joint is covered by the neck portion of the cuff and radially inside the neck portion.

5. The tracheal ventilation apparatus according to claim 2, characterised in that the joint is formed from a part of the wall of a neck section of the cuff.

6. The tracheal ventilation apparatus according to claim 1, characterised in that the joint is one or both of elastically expandable and elastically compressible in the longitudinal direction of the cannula tube.

7. The tracheal ventilation apparatus according to claim 2, characterised in that the joint forms at least a part of the inner wall of the cuff.

8. The tracheal ventilation apparatus according to claim 1, characterised in that a change in the gap width of the annular gap between the proximal tube portion and the distal tube portion in an event of an elastic deformation of the joint is 1 mm to 10 mm.

9. The tracheal ventilation apparatus according to claim 1, characterised in that the distal tube portion has a maximum bending angle relative to the longitudinal axis of the proximal tube portion by way of the joint of +10° to −10°.

10. The tracheal ventilation apparatus according to claim 1, characterised in that the joint angle between the proximal tube portion and the distal tube portion is changeable by up to 10°.

11. The tracheal ventilation apparatus according to claim 1, wherein the cannula tube and the sleeve portion are each made of a plastic, characterised in that the sleeve portion has a lower shore hardness than the cannula tube, the sleeve portion connecting the proximal tube portion to the distal tube portion.

12. The tracheal ventilation apparatus according to claim 11, wherein the sleeve portion includes a second sleeve portion arranged concentrically with respect to a first sleeve portion, wherein the first sleeve portion is connected to the proximal tube portion and the distal tube portion radially on an outside, and the second sleeve portion is connected to the proximal tube portion and the distal tube portion radially on an inside.

13. The tracheal ventilation apparatus according to claim 12, characterised in that one or both of the first sleeve portion and the second sleeve portion overlap with the proximal and the distal tube portions.

14. The tracheal ventilation apparatus according to claim 11, characterised in that the first sleeve portion and/or the second sleeve portion has a reduced wall thickness compared with the average wall thickness of the proximal tube portion in the connection region of the joint, wherein the reduced wall thickness is 0.1 mm to 0.4 mm.

15. The tracheal ventilation apparatus according to claim 1, characterised in that the sleeve portion connects the proximal tube portion and the distal tube portion to one another in a flush manner.

16. The tracheal ventilation apparatus according to claim 1, characterised in that the joint has a plurality of plastic struts which connect the proximal tube portion to the distal tube portion.

17. The tracheal ventilation apparatus according to claim 1, characterised in that the gap width of the annular gap is 1 mm to 10 mm.

18. The tracheal ventilation apparatus according to claim 1, characterised in that the joint is one or more of adhesively bonded, welded and injection-moulded to one or both of the proximal tube portion and the distal tube portion.

19. The tracheal ventilation apparatus according to claim 3, characterised in that the wall thickness of the portion adjoining the central portion is 50% to 300% greater than the wall thickness of the central portion.

20. The tracheal ventilation apparatus according to claim 8, characterised in that the change in the gap width of the annular gap between the proximal tube portion and the distal tube portion is 2 mm to 4 mm.

21. The tracheal ventilation apparatus according to claim 9, characterised in that the maximum bending angle relative to the longitudinal axis of the proximal tube portion by way of the joint is +25° to −25°.

22. The tracheal ventilation apparatus according to claim 13, characterised in that an overlap region on each side of the gap is 2 mm to 6 mm.

23. The tracheal ventilation apparatus according to claim 17, characterised in that the gap width of the annular gap is 2 mm to 4 mm.

* * * * *